United States Patent [19]
Gerson

[11] Patent Number: 5,562,093
[45] Date of Patent: Oct. 8, 1996

[54] MOUTH-TO-MOUTH RESUSCITATION BARRIER

[76] Inventor: Howard J. Gerson, 5300 W. 131st Ter., Overland Park, Kans. 66209

[21] Appl. No.: 523,954

[22] Filed: Sep. 6, 1995

[51] Int. Cl.⁶ ............................................. A61M 16/00
[52] U.S. Cl. ........................ 128/203.11; 128/202.28; 128/202.29; 128/205.24
[58] Field of Search .................. 128/202.27, 202.28, 128/202.29, 203.11, 205.24

[56] References Cited

U.S. PATENT DOCUMENTS

| | | | |
|---|---|---|---|
| 2,995,131 | 8/1961 | Elam et al. | 128/202.28 |
| 3,021,836 | 2/1962 | Marsden | 128/202.28 |
| 3,057,347 | 10/1962 | McGee | 128/202.28 |
| 3,137,293 | 6/1964 | Green | 128/202.28 |
| 3,303,845 | 2/1967 | Detmer, III | 128/202.28 |
| 3,387,624 | 6/1968 | Soucy | 137/847 |
| 3,407,810 | 10/1968 | Waldrep | 128/202.28 |
| 3,473,532 | 10/1969 | Eisenberg | 604/262 |
| 3,518,989 | 7/1970 | Seeler | 128/202.28 |
| 3,626,936 | 12/1971 | Barker | 128/202.28 |
| 3,724,461 | 4/1973 | Eisenberg | 604/262 |
| 3,802,428 | 4/1974 | Sherman | 128/202.28 |
| 3,957,046 | 5/1976 | Harris | 128/203.11 |
| 4,360,017 | 11/1982 | Barlett | 128/202.28 |
| 4,535,765 | 8/1985 | Paoluccio et al. | 128/203.11 |
| 4,579,114 | 4/1986 | Gray et al. | 128/203.11 |
| 4,607,663 | 8/1986 | Raftis et al. | 137/846 |
| 4,622,964 | 11/1986 | Flynn | 128/205.24 |
| 4,697,587 | 10/1987 | Marinkovich | 128/203.11 |
| 4,819,627 | 4/1989 | Connors | 128/202.28 |
| 4,819,628 | 4/1989 | Eisenberg et al. | 128/203.11 |
| 4,858,605 | 8/1989 | Levy | 128/203.11 |
| 4,909,245 | 3/1990 | Wollenhaupt | 128/203.11 |
| 4,969,456 | 11/1990 | Cooper | 128/203.11 |
| 5,119,809 | 6/1992 | Gerson | 128/203.11 |

FOREIGN PATENT DOCUMENTS

| | | | |
|---|---|---|---|
| 240878 | 10/1962 | Australia | 128/202.28 |
| 303367 | 2/1989 | European Pat. Off. | 128/203.11 |
| 1204930 | 1/1960 | France . | |
| 1183054 | 3/1970 | United Kingdom | 128/203.11 |
| 2204498 | 11/1988 | United Kingdom | 128/203.11 |

Primary Examiner—Vincent Millin
Assistant Examiner—V. Srivastava
Attorney, Agent, or Firm—Litman, McMahon and Brown, LLC

[57] ABSTRACT

A mouth-to-mouth barrier for facilitating mouth-to-mouth resuscitation of a heart attack or accident victim or the like while protecting a rescuer, includes a transparent shield and a breathing tube extending through an opening in the shield. Within the tube, an air passage is defined by a generally cylindrical inner wall. The inner wall forms an upper cylinder of a first diameter and then the inner wall then tapers outward toward an outer wall to form a lower cylinder of a second diameter which is larger in diameter than the upper cylinder. A retaining ring is snapped into place within the lower cylinder which ring serves as a keeper to hold a generally conical valve member in place within the lower cylinder. The valve member is thus movable between a rest, open position atop the ring and a closed position in which it abuts the tapered portion of the inner wall. A cross-shaped portion of the valve member, along with a cross grid formed in the retaining ring allow a large volume of air to flow through the barrier when the valve is open, yet acts as a very fast acting one-way check valve which is positioned a maximum distance from the rescuer's mouth and which prevents a victim from exhaling into the rescuer's mouth.

17 Claims, 2 Drawing Sheets

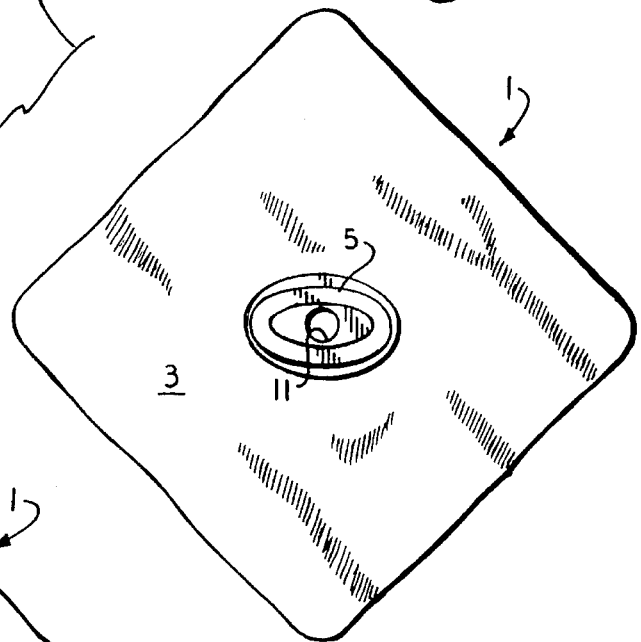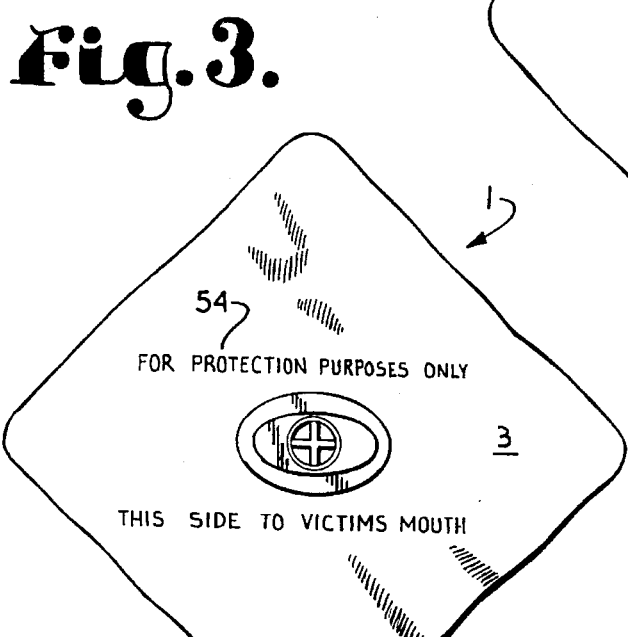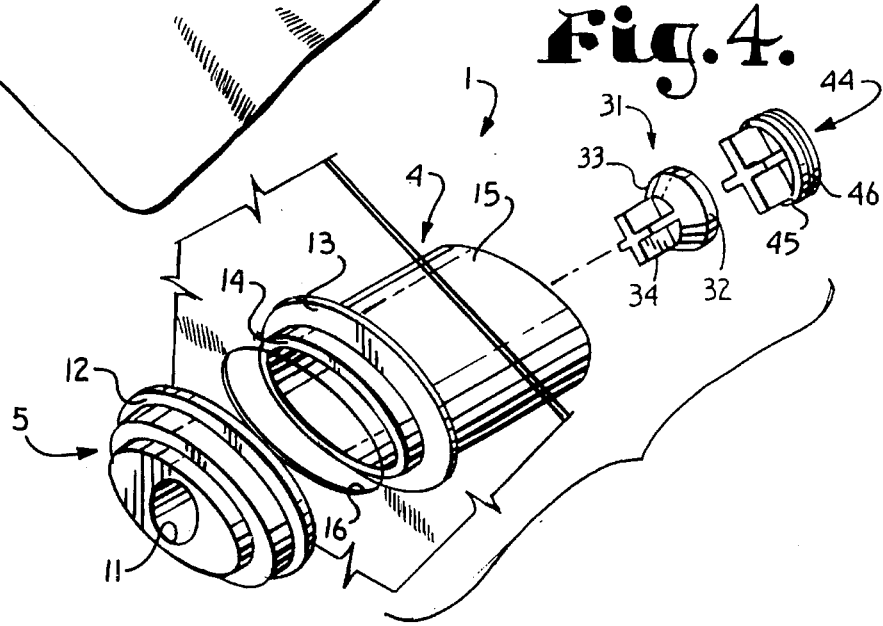

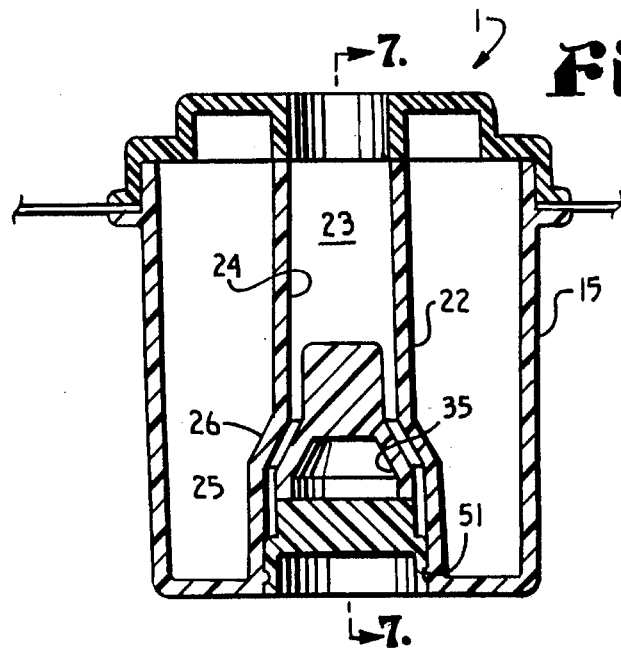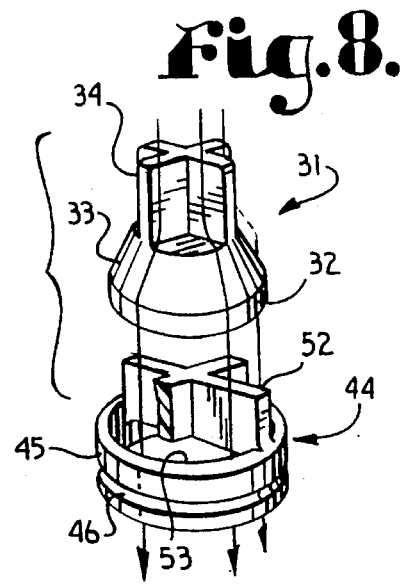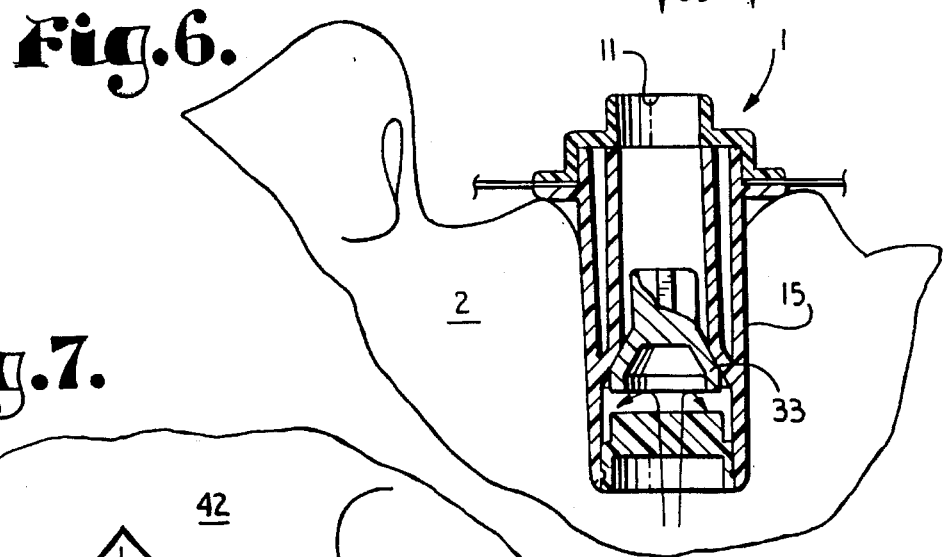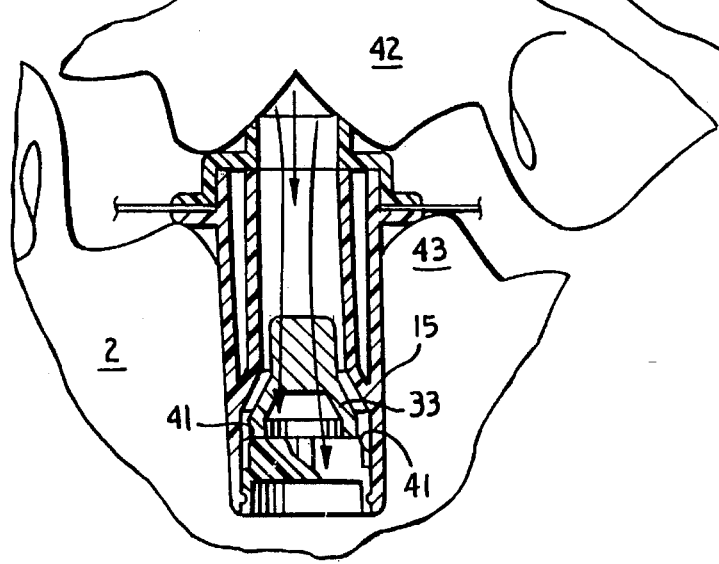

MOUTH-TO-MOUTH RESUSCITATION BARRIER

BACKGROUND OF THE INVENTION

The present invention relates to an improved mouth-to-mouth barrier for facilitating mouth-to-mouth resuscitation of a victim who has stopped breathing and for protecting a rescuer engaged in such mouth-to-mouth resuscitation.

Recent widespread dissemination of information and training courses for cardiopulmonary resuscitation (CPR) by the International Red Cross and other organizations has done much to promote the widespread use of this vital life saving technique. CPR, of course, is a technique which combines chest massage with mouth-to-mouth resuscitation in an attempt to revive a victim's interrupted heartbeat and breathing.

Unfortunately, persons conducting CPR are likely to catch communicable diseases from the victim and with the increased number of Acquired Immune Deficiency Syndrome (AIDS) victims which may have blood or other infected body fluids in their mouths, CPR trained individuals and even professional medical practitioners have become reluctant to use mouth-to-mouth resuscitation techniques. This is especially due to the widespread fear, whether justified or not, that the AIDS virus can be transmitted through mouth-to-mouth contact. Nevertheless, when blood is present, there is little doubt that contamination can occur. In addition to the fear of contracting AIDS or other communicable diseases, ordinary personal hygiene considerations often delay or prevent timely mouth-to-mouth resuscitation. Numerous devices have been designed in an effort to overcome these problems.

One approach has been to use an air permeable cloth or mesh which is placed over the victim's mouth prior to giving him mouth-to-mouth resuscitation. These devices have tended to impede the flow of air from the rescuer to the victim and limit the effectiveness of resuscitation efforts.

Another approach has been to use an elongated hollow tube which is open at both ends. One end is placed in the victim's mouth while the rescuer places his mouth over the other open end and exhales through the tube to force air into the victim's lungs. While generally an improvement over an air permeable cloth, this approach does not prevent saliva or other liquids or solids from being passed from the victim through the tube to the rescuer.

The effectiveness of these elongated tubes has been enhanced by placing a protective shield around the tubes and by putting one-way check valves inside the tubes. The combination of an extended shield and a one-way valve has greatly reduced the chances of exposure to communicable diseases by a potential rescuer. By making these protective shield and valve equipped tube devices disposable, personal hygiene concerns have also been largely mitigated. Several problems with this basic arrangement remain, however. The hollow tubes have tended to be too flexible, and are thus subject to being closed off if a victim bites down on the tube. The tube's effectiveness can also be compromised if a victim's tongue or any other solid object enters the open end of the tube and blocks the airflow. Furthermore, check valves have generally consisted of flexible flaps which are attached at one end to a portion of the elongate tube, which flaps have tended to be relatively slow in closing. The lack of readily available instructions on the proper use of these devices has also been a drawback.

One attempt to address these problems is described in U.S. Pat. No. 5,119,809 of Howard Gerson, which issued Jun. 9, 1992 and which is entitled MOUTH-TO-MOUTH WITH VALVE AND BARRIER ("the '809 patent"). The '809 patent teaches a mouth-to-mouth barrier with a transparent shield and a breathing tube extending through an opening in the shield. A light weight air impermeable plate valve is positioned within the breathing tube and is free to move between a lower position which permits air to flow from the rescuer around the plate and through the breathing tube and an upper position which blocks airflow from the victim back towards the rescuer. The breathing tube has a plurality of longitudinally extending strengthening ribs and an integrally molded grid on the bottom thereof to strengthen and rigidize the structure.

While the barrier described in the '809 patent performs generally satisfactorily, a number of problems remain. Assembly of the barrier is difficult since the movable plate valve must be inserted within the breathing tube and the shield must be simultaneously seated on a flange surrounding the breathing tube before the mouthpiece is attached in place. Precise positioning of the plate valve is essential for proper operation, yet no guides or channels are provided to facilitate correct valve placement. Furthermore, the movable valve in the barrier is positioned immediately adjacent the rescuer's mouth. Thus, virtually the entire breathing tube can be filled with contaminated saliva from the victim should the victim suddenly exhale or cough and any momentary failure of the valve would immediately expose the rescuer to the victim's potentially contaminated saliva and or blood.

It is clear then, that a need exists for a reliable, one-way valve and shield equipped mouth-to-mouth resuscitation barrier which avoids the above cited drawbacks. Such a device should be simple and inexpensive to produce and easy to assemble, and, preferably, should place the valve at a maximum distance away from the rescuer's mouth.

SUMMARY OF THE INVENTION

The present invention is a mouth-to-mouth barrier for facilitating mouth-to-mouth resuscitation while affording effective protection to a person giving such mouth-to-mouth resuscitation. The barrier comprises an elongate hollow breathing tube with a continuous outer wall which is preferably elliptical in cross-section to simulate the shape of a typical mouth. An external ledge is formed around the circumference of the outer wall near the top of the elongate breathing tube. The top of the breathing tube is then placed through an opening near the center of a protective transparent shield which extends for a considerable distance on all sides of the elongate breathing tube. A mouthpiece fits snugly over the top of the breathing tube and is attached to the ledge to securely retain the mouthpiece and the shield in place. Within the elliptical breathing tube, an air passage is defined by a generally cylindrical inner wall. The inner wall forms an upper cylinder of a first diameter which extends approximately two-thirds of the way down the breathing tube. The inner wall then tapers outward toward the outer wall to form a lower cylinder of a second diameter which is larger in diameter than the upper cylinder. A peripheral projection extends inward within the lower cylinder such that a retaining ring with a matching peripheral indentation can be snapped into place within the lower cylinder. The retaining ring includes a cross grid integrally formed therewith which serves as a rest and a keeper to hold a valve member with a generally frusto-conical base in place within the lower cylinder. The retaining ring and the cross grid also serve to rigidize the breathing tube to prevent it's collapse should the victim inadvertently bite down on the tube. The valve member is movable between a rest, open position atop the cross grid and a closed position in which it abuts the tapered portion of the inner wall. The base of the valve member is preferably hollow and the valve member also includes a cross-shaped portion extending upward from the base which serves as a guide. Assembly of the inventive barrier simply involves placing the transparent shield over the ledge near the top of the breathing tube and attaching the mouthpiece over it and onto the ledge. The conical valve member is then placed in the bottom of the breathing tube with the cross-shaped portion serving as a guide to center the valve member within the breathing tube. The retaining ring is then snapped into place on the tube bottom, and the mouthpiece and/or the retaining ring can be ultrasonically welded or otherwise adhered in place. The cross-shaped valve portion, along with the cross grid formed in the retaining ring, collectively allow a large volume of air to flow through the barrier when the valve is open. The light weight valve member in combination with the cylindrical inner walls forms a very fast acting one-way check valve which is positioned a maximum distance from the rescuer's mouth and which prevents a victim from exhaling into the rescuer's mouth. The extended shield directs air and any other matter exhaled or coughed up by the victim away from the face of the rescuer and the shield provides a convenient place for instructions and other indicia to be printed.

OBJECTS AND ADVANTAGES OF THE INVENTION

The principal objects of the present invention are: to provide an improved mouth-to-mouth barrier for facilitating the resuscitation of an accident or heart attack victim; to provide such a barrier which is light weight and inexpensive to produce; to provide such a barrier which is disposable after use; to provide such a barrier which has an effective, fast acting one-way check valve positioned a maximum distance from the rescuer's mouth for effectively preventing the victim from exhaling or coughing into the mouth of the rescuer; to provide such a barrier which has an extended transparent shield surrounding an elongate breathing tube incorporating the check valve, which shield prevents the victim from exhaling or otherwise expelling saliva or other material onto the rescuer; to provide such a barrier which is easily assembled, in which the valve member is readily and conveniently positioned within the breathing tube, and which, when the valve is opened, allows a large volume of air to flow from the rescuer into the victim's mouth; to provide such a barrier in which the elongate breathing tube has a retaining ring with a cross grid integrally formed therein which is snapped into a lower opening in the breathing tube; and to provide such an improved barrier which is particularly well adapted for its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a victim with an improved mouth-to-mouth barrier in accordance with the present invention shown inserted into her mouth.

FIG. 2 is an enlarged top plan view of the improved mouth-to-mouth barrier, illustrating a mouthpiece with a circular opening.

FIG. 3 is an enlarged bottom plan view of the improved mouth-to-mouth barrier, illustrating the cross grid formed in the retaining ring and showing instruction indicia printed on an extended shield.

FIG. 4 is an enlarged, exploded perspective view of the improved mouth-to-mouth barrier including an elongate breathing tube, a one-way check valve and retaining ring, a mouthpiece and a fragmented view of the shield.

FIG. 5 is a greatly enlarged, cross-sectional view of the improved mouth-to-mouth barrier, taken along line 5—5 of FIG. 2, and illustrating the one way valve member in an open position.

FIG. 6 is an enlarged, cross-sectional view of the improved mouth-to-mouth barrier, taken along line 7—7 of FIG. 5, but illustrating the one-way valve in a closed position to block air flow from the victim's mouth.

FIG. 7 is an enlarged, cross-sectional view of the improved mouth-to-mouth barrier, also taken along line 7—7 of FIG. 5, and illustrating the one-way valve member in an open position to allow air flow from the rescuer's mouth to the victim's mouth.

FIG. 8 is an enlarged, perspective view of the movable valve member and the retaining ring and integral cross grid.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to FIG. 1, there is shown an improved mouth-to-mouth resuscitation barrier 1 in accordance with the present invention, placed in the mouth of an inert victim 2 and ready for use in mouth-to-mouth resuscitation of the victim 2. The barrier 1 includes a transparent shield 3 which covers a substantial portion of the victim's face and an elongate breathing tube 4 (FIG. 4), which is preferably elliptical in cross section and which is of a length which extends substantially into the mouth of the victim 2. The breathing tube 4 separates the victim's lips and teeth to form an effective airway, as shown in FIGS. 7 and 8. It should be noted that the barrier 1 is not necessarily drawn to scale in FIGS. 2–8, but the relative sizes of different components may be exaggerated for ease of illustration. The breathing tube 4, for example, can be 2 to 3 cm in overall length, although, in the United States, recent FDA regulations limit the length to 2 cm or less for over-the-counter distribution. An oval mouthpiece 5 is attached to the elongate breathing tube 4 and is clearly visible in FIG. 1. The oval mouthpiece 5 has an opening 11 formed therein for passage of air into the elongate breathing tube 4 and includes a peripheral shoulder 12 which is sized and positioned to match a circumferential ledge 13 which surrounds an upper portion 14 of an outer wall 15 of the elongate breathing tube 4. The transparent shield 3 has an ovate center cut-out 16 which is sized to fit over the upper portion 14 of the breathing tube 4. Once the mouthpiece 5 is positioned over the upper portion 14 of the breathing tube 4, the transparent shield 3 is sandwiched between and held in place by the shoulder 12 of the mouthpiece 5 and the circumferential ledge 13 extending around the breathing tube outer wall 15.

Referring to FIGS. 4–8, the outer wall 15 of the breathing tube 4 is preferably elliptical in cross section. An inner wall 22 is positioned within the outer wall 15 and forms an air passage 23 with a generally cylindrical upper portion 24 of a first diameter and a generally cylindrical lower portion 25 of a second, larger diameter. The air passage 23 is also formed by a tapered section 26 of the inner wall 22 which transitions between the upper portion 24 and the lower portion 25.

A valve member 31 includes a base 32 with a generally frusto-conical portion 33 and an integrally formed cross-shaped portion 34. The base 32 preferably includes a hollow center section 35 for weight reduction, as well as to provide a scooping action for air exhaled by the victim 2. The cross-shaped portion 34 acts as a guide, as will be explained below. The valve member 31 is sized to fit within the lower cylindrical portion 25 of the air passage 23, while leaving a peripheral gap 41 between the base portion 32 and the frusto-conical portion 33 and the inside surface of the inner wall 22 which allows the passage of a considerable air flow from a rescuer's mouth 42 to the victim's mouth 43, as illustrated in FIG. 7.

A retaining ring 44 includes a lower ring member 45 with a peripheral indentation 46 formed therein which is sized to mate with a peripheral projection 51 (FIG. 5) which extends about the inner periphery of the lower cylindrical portion 25 of the air passage 23. The retaining ring 44 can thus be snapped into place within the lower air passage portion 25. The retaining ring 44 also includes an integrally formed cross grid 52 which forms a base upon which the valve member 31 rests in the open position but which also allows substantial air flow through gaps 53 in the cross grid. The cross grid 52, which can be molded along with the lower ring member 45, also serves to rigidize the lower portion of the breathing tube 4 such that, should the victim 2 inadvertently bite down on the breathing tube 4, the breathing tube 4 will not collapse and stop the flow of air therethrough. Finally, the cross grid 52 acts to prevent the victim 2 from inserting his or her tongue fully into the breathing tube 4 which could result in total blockage of air from the rescuer and prevents the introduction of large solids into the barrier 1 which could interfere with the action of the barrier 1.

Assembly of the improved mouth-to-mouth barrier 1 simply involves placing the ovate opening 16 of the transparent shield 3 over the upper portion 14 of the breathing tube 4. The mouthpiece 5 is then placed over the tube upper portion 14, thus confining the shield 3 between the shoulder 12 of the mouthpiece 5 and the ledge 13 surrounding the outer wall 15 in the upper portion 14 of the breathing tube 4. Once the barrier 1 is fully assembled, the mouthpiece 5 is preferably ultrasonically welded in position on the top of the breathing tube 4, but attachment with an adhesive is an alternative. Alternatively, the shield 3 can be held in place via a separate snap ring (not shown). Next, the barrier 1 is turned over and the valve member 31 is inserted into the air passage lower portion 25 such that the cross-shaped portion 34 extends into the upper air passage 24. The retaining ring 44 is then simply snapped into place within the air passage lower portion 25 to retain the valve member 31 in place within the barrier 1. The cross-shaped valve member portion 34 serves as a guide to allow precise placement of the valve member 31 within the breathing tube 4 prior to placement of the retaining ring 44 onto the tube 4.

In operation, the assembled barrier 1 is first inserted into an inert victim's mouth 43, as illustrated in FIGS. 1 and 6. A rescuer then places his or her mouth 42 over the mouthpiece 5 and breathes outward, as shown in FIG. 7. The rescuer's breath forces the valve member 31 to the open position, again as shown in FIG. 7, allowing air from the rescuer 42 to flow through the breathing tube 4 to the victim 2 via the resulting air gaps 41 which extend peripherally around the valve member 31. Should the victim 2 cough or suddenly exhale, as shown in FIG. 6, air from the victim's mouth virtually instantaneously forces the valve member 31 upward such that the tapered portion 33 of the valve member 31 abuts the tapered section 26 of the inner wall 22 of the breathing tube 4. The cross-shaped portion 34 of the valve member 31 again acts as a guide to insure that the valve member 31 is oriented correctly relative to the inner wall 22 of the air passage 23 as it moves up and down therein. The valve member 31, in the upper, closed position of FIG. 6, thus provides an effective seal, preventing the transfer of air, and accompanying bodily fluids, from the victim's mouth 43 to the rescuer's mouth 42. It should be noted that, in the improved barrier 1, the valve member 31 is positioned close to the victim's mouth, and thus is located a maximum distance from the rescuer's mouth 42. This provides increased safety and protection of the rescuer from any inadvertent transmission of bodily fluids from the victim 2.

The transparent shield 3 is preferably made of a flexible plastic material such as a film-forming thermoplastic which is generally impermeable to ordinary bodily fluids. Examples of such material include polyvinyl chlorides, polyethylene, polypropylene, etc. The breathing tube 4 including the inner wall 15, as well as the mouthpiece 5 and the retaining ring 44, are preferably formed of a rigid molded plastic. The valve member 31 is preferably formed of a synthetic rubber material, or, alternatively, can be formed of a resilient foam material or any other suitable material which would form a tight seal in the closed position of FIG. 6. After assembly, the mouthpiece 5 and/or the retaining ring 44 can be ultrasonically welded into place on the breathing tube 4. The shield 3 is a convenient place to print instructional or other indicia, such as the message 54 (FIG. 3).

While the transparent shield 2 has been illustrated as generally square or diamond shaped, it should be apparent that other shapes such as a circle or an ellipse could be equally effective. Furthermore, the cross-sectional shape of the breathing tube 4, the mouthpiece 5, the air passage 23, the valve member 31, the retaining ring 44, etc. are merely illustrative and other shapes can be effectively used.

It is to be understood that while certain forms of the present invention have been illustrated and described herein, it is not to be limited to the specific forms or arrangement of parts described and shown.

What is claimed and desired to be secured by Letters Patent is as follows:

1. An improved mouth-to-mouth resuscitation barrier comprising:
   (a) an elongate breathing tube with upper and lower openings;
   (b) an air passage formed within said breathing tube and extending between said upper and lower openings, said air passage including an upper portion of a first diameter and a lower portion of a second, larger diameter;
   (c) a valve member movable within said air passage between a lower, open position in which air can flow from said upper portion to said lower portion of said air passage and an upper, closed position in which air cannot flow from said lower portion to said upper portion of said air passage; and (d) a retaining ring, said retaining ring including a ring portion sized to fit snugly within the lower opening of said breathing tube and a cross grid portion which is positioned to support said valve member in said open position while allowing substantial air flow therethrough.

2. An apparatus as in claim 1, and further comprising:

(a) a ledge formed about the outside periphery of said breathing tube proximate the upper opening thereof;

(b) a protective shield with a central opening sized to fit over said breathing tube but not over said ledge; and (c) a mouthpiece sized to fit over the upper opening of said breathing tube and with a shoulder sized to mate with said ledge to thereby secure said protective shield therebetween.

3. An apparatus as in claim 1, and wherein said valve member comprises:

(a) a base including a frusto-conical section; and (b) a cross-shaped portion which extends upward from said base and into said upper portion of said air passage to act as a guide for said valve member during assembly and operation of said barrier.

4. An apparatus as in claim 3, and wherein the base of said valve member includes a hollow center section.

5. An apparatus as in claim 1, and wherein:

(a) said breathing tube is formed by an outer wall which is generally elliptical in cross section; and (b) an inner wall which forms said air passage, said inner wall having a generally cylindrical upper portion of said first diameter to form said upper portion of said air passage; an intermediate tapered section which gradually increases in diameter; and a generally cylindrical lower portion of said second diameter to form said lower portion of said air passage.

6. An apparatus as in claim 1, and wherein:

(a) said breathing tube includes a peripheral projection positioned proximate the lower opening thereof, said projection extending inward into said air passage; and (b) said retaining ring includes a peripheral indentation surrounding said ring portion, said indentation being sized and positioned to mate with said peripheral projection in said breathing tube when said retaining ring is placed within said lower opening.

7. An improved mouth-to-mouth resuscitation barrier comprising:

(a) an elongate breathing tube with upper and lower openings;

(b) an air passage formed within said breathing tube and extending between said upper and lower openings, said air passage including an upper portion of a first diameter and a lower portion of a second, larger diameter;

(c) a valve member movable within said air passage between a lower, open position in which air can flow from said upper portion to said lower portion of said air passage and an upper, closed position in which air cannot flow from said lower portion to said upper portion of said air passage, said valve member including:

(i) a base including a frusto-conical section; and (ii) a cross-shaped portion which extends upward from said base and into said upper portion of said air passage to act as a guide for said valve member during assembly and operation of said barrier; and (d) a retaining ring sized to fit snugly within the lower opening of said breathing tube to retain said valve member therein.

8. An apparatus as in claim 7, and further comprising:

(a) a ledge formed about the periphery of said breathing tube proximate the upper opening thereof (b) a protective shield with a central opening sized to fit over said breathing tube but not over said ledge; and (c) a mouthpiece sized to fit over the upper opening of said breathing tube and with a shoulder sized to mate with said ledge to thereby secure said protective shield therebetween.

9. An apparatus as in claim 7, and wherein said retaining ring comprises:

(a) a ring portion sized to fit snugly within the lower opening of said breathing tube; and (b) a cross grid portion extending upward from said ring portion, said cross grid portion being positioned to support said valve member in said open position while allowing substantial air flow therethrough.

10. An apparatus as in claim 9, and wherein:

(a) said breathing tube includes a peripheral projection positioned proximate the lower opening thereof, said projection extending inward into said air passage; and (b) said retaining ring includes a peripheral indentation surrounding said ring portion, said indentation being sized and positioned to mate with said peripheral projection in said breathing tube when said retaining ring is placed within said lower opening.

11. An apparatus as in claim 7, and wherein the base of said valve member includes a hollow center section.

12. An apparatus as in claim 7, and wherein:

(a) said breathing tube is formed by an outer wall which is generally elliptical in cross section; and (b) an inner wall which forms said air passage, said inner wall having a generally cylindrical upper portion of said first diameter to form said upper portion of said air passage; a tapered section which gradually increases in diameter; and a generally cylindrical lower portion of said second diameter to form said lower portion of said air passage.

13. An improved mouth-to-mouth resuscitation barrier comprising:

(a) an elongate breathing tube with upper and lower openings;

(b) an air passage formed within said breathing tube and extending between said upper and lower openings, said air passage including an upper portion of a first diameter and a lower portion of a second, larger diameter;

(c) a valve member movable within said air passage between a lower, open position in which air can flow from said upper portion to said lower portion of said air passage and an upper, closed position in which air cannot flow from said lower portion to said upper portion of said air passage, said valve member including:

(i) a base including a frusto-conical section; and (ii) a cross-shaped portion which extends upward from said base and into said upper portion of said air passage to act as a guide for said valve member during assembly and operation of said barrier; and (d) a retaining ring sized to fit snugly within the lower opening of said breathing tube to retain said valve member therein, said retaining ring comprising:

(i) a ring portion sized to fit snugly within the lower opening of said breathing tube; and (ii) a cross grid portion extending upward from said ring portion, said cross grid portion being positioned to support said valve member in said open position while allowing substantial air flow therethrough.

14. An apparatus as in claim 13, and further comprising:

(a) a ledge formed about the periphery of said breathing tube proximate the upper opening thereof (b) a protective shield with a central opening sized to fit over said breathing tube but not over said ledge; and (c) a mouthpiece sized to fit over the upper opening of said breathing tube and with a shoulder sized to mate with said ledge to thereby secure said protective shield therebetween.

15. An apparatus as in claim 13, and wherein the base of said valve member includes a hollow center section.

16. An apparatus as in claim 13, and wherein:

(a) said breathing tube is formed by an outer wall which is generally elliptical in cross section; and (b) an inner wall which forms said air passage, said inner wall having a generally cylindrical upper portion of said first diameter to form said upper portion of said air passage; a tapered section which gradually increases in diameter; and a generally cylindrical lower portion of said second diameter to form said lower portion of said air passage.

17. An apparatus as in claim 13, and wherein:

(a) said breathing tube includes a peripheral projection positioned proximate the lower opening thereof, said projection extending inward into said air passage; and (b) said retaining ring includes a peripheral indentation surrounding said ring portion, said indentation being sized and positioned to mate with said peripheral projection in said breathing tube when said retaining ring is placed within said lower opening.

* * * * *